US010600274B2

(12) United States Patent
Witczak

(10) Patent No.: US 10,600,274 B2
(45) Date of Patent: Mar. 24, 2020

(54) DEVICE FOR THE AUTOMATIC AND INSTANT DETECTION OF MOVEMENT OF AN OBJECT

(71) Applicant: Medsecure Solutions Inc., Trois-Rivières (CA)

(72) Inventor: John Witczak, Faulx-les-Tombes (BE)

(73) Assignee: MEDSECURE SOLUTIONS INC., Trois-Rivieres (CA)

( * ) Notice: Subject to any disclaimer, the term of this patent is extended or adjusted under 35 U.S.C. 154(b) by 0 days.

(21) Appl. No.: 15/948,363

(22) Filed: Apr. 9, 2018

(65) Prior Publication Data

US 2019/0019369 A1 Jan. 17, 2019

Related U.S. Application Data

(60) Provisional application No. 62/482,898, filed on Apr. 7, 2017.

(51) Int. Cl.
| | |
|---|---|
| *G06F 7/00* | (2006.01) |
| *G07F 17/00* | (2006.01) |
| *A61J 1/03* | (2006.01) |
| *G16H 20/10* | (2018.01) |
| *G07F 11/44* | (2006.01) |
| *G07F 11/02* | (2006.01) |
| *G07F 11/62* | (2006.01) |
| *A61J 7/00* | (2006.01) |
| *G07F 15/00* | (2006.01) |

(52) U.S. Cl.
CPC ............ *G07F 17/0092* (2013.01); *A61J 1/03* (2013.01); *G07F 11/02* (2013.01); *G07F 11/44* (2013.01); *G07F 11/62* (2013.01); *G16H 20/10* (2018.01); *A61J 7/0084* (2013.01); *G07F 15/00* (2013.01)

(58) Field of Classification Search
None
See application file for complete search history.

(56) References Cited

U.S. PATENT DOCUMENTS

| | | | | |
|---|---|---|---|---|
| 2,761,559 | A * | 9/1956 | Burge | H02B 3/00 |
| | | | | 209/573 |
| 6,396,401 | B1 * | 5/2002 | Matsuo | G08B 13/1454 |
| | | | | 340/568.1 |
| 2007/0221680 | A1 | 9/2007 | Yuyama | |
| 2010/0228149 | A1 * | 9/2010 | Fujimura | A61B 5/14532 |
| | | | | 600/583 |
| 2017/0323512 | A1 * | 11/2017 | Fukuda | G07F 11/24 |
| 2018/0022232 | A1 * | 1/2018 | Kawahira | B60N 2/90 |
| | | | | 73/862.628 |
| 2018/0072186 | A1 * | 3/2018 | Nakazaki | B60N 2/90 |

FOREIGN PATENT DOCUMENTS

| | | |
|---|---|---|
| EP | 1118318 A2 | 7/2001 |
| EP | 1923034 A1 | 5/2008 |

* cited by examiner

*Primary Examiner* — Yolanda R Cumbess
(74) *Attorney, Agent, or Firm* — Cantor Colburn LLP

(57) ABSTRACT

Device including an object accommodating system having two flaps defining between one another an accommodating space and bearing against a plate of a pushbutton arranged to move between a first position corresponding to the placing of the object in the accommodating space, this causing the ends of the flaps to move away from one another, and a second position corresponding to the removal of the object, this causing the two ends to move towards one another, the plate being connected to a compression spring bearing against a bottom wall of a housing.

14 Claims, 3 Drawing Sheets

DEVICE FOR THE AUTOMATIC AND INSTANT DETECTION OF MOVEMENT OF AN OBJECT

CROSS REFERENCE TO RELATED APPLICATION

This application is related to and claims the benefit of U.S. Provisional Patent Application Ser. No. 62/482,898 filed on Apr. 7, 2017, the contents of which are herein incorporated by reference in their entirety.

TECHNICAL FIELD

The present disclosure relates to a device for the automatic and instant detection of movement of an object comprising a housing in which is arranged an object accommodating system that comprises a first and a second flap facing one another, each flap comprising a first movable part, the first movable parts being arranged so as to define between one another an object accommodating space defined by a predetermined accommodating volume, each movable part having a first fixed end and, at its second end, bearing against a means of pressing a pushbutton arranged to move along a vertical axis between a first position resulting from the placing of an object in the accommodating space causing the two ends to move away from one another, and a second position resulting from the removal of the object from the accommodating space causing the two ends to move towards one another.

The present disclosure has applications more particularly in the medical field relating to complete drug management.

More particularly, the present disclosure, once combined with a pressure sensor, provides a drug management system in a hospital environment that is completely automated, thus avoiding any manual intervention particularly as regards billing the patients for these drugs. Ideally, this system enables automation not only in monitoring the stock of drugs in local pharmacies but also in recording the drugs taken from these pharmacies in order to supply a patient.

BACKGROUND

Such a device is in fact known for example from document EP1923034A1, which discloses a spring system accommodated in a support block. This spring system is formed of two symmetrical flaps preferably made of a flexible polymer material and each formed of an upper wing and a lower wing articulated to one another and when at rest forming an obtuse angle. These flaps are also positioned back-to-back at their articulation and the upper wings are configured to form an accommodating space for the object. The lower wings are connected to one another by a torsion spring that cooperates with a pushbutton arranged to move perpendicular to a pressure sensor until coming into contact therewith or releasing itself therefrom.

The introduction of an object into the accommodating space, for example a vial of an injectable pharmaceutical solution, causes the upper wings, the first ends of which are fixed because they are connected to the support block by means of lugs and slots, to move apart. Since the first ends are fixed, the moving apart of the upper wings causes a moving apart in a horizontal direction of their movable second ends which, by means of the articulation, is transmitted to each of the two flap wings, these second flap wings being connected at two free ends of the torsion spring by hooks on each of the movable ends of the second wings, so that the moving apart of these two movable ends is converted by means of the tension of the torsion spring into a vertical force acting on the pushbutton. The pushbutton then moves in the direction of the pressure sensor until it comes into contact therewith when the torsion spring is in its pushed position, which causes the emission of a first electrical impulse translating this movement of introduction and, consequently, the presence of this object in the accommodating space, said first impulse being processed by a processing means arranged to convert this first impulse into a signal indicating the presence of the object in the accommodating space.

By contrast, the removal of an object from its accommodating space causes the upper wings to move towards one another in a horizontal direction, due to the release of the tension of the spring that is in a rest position (i.e. in a position where the torsion spring is in a rest state and therefore undergoes no torsion tension) and simultaneously that of the contact of the pushbutton with the pressure sensor. This pushbutton then moves away from this sensor causing the emission of a second electrical impulse indicating that this movement has occurred and, consequently, that this object is absent from the accommodating space, said second impulse being processed by the processing means arranged to convert this second impulse into a signal indicating the absence of the object in the accommodating space.

These electrical impulses, which constitute data concerning the movement of these objects, can be transmitted, depending on requirements, via an electronic card and for example a Wi-Fi network, for example to a computer processing unit for their use by the appropriate software.

The vertical movement of the pushbutton is guided by the presence of longitudinal raised portions that cooperate with the slots present on a tubular portion in which the pushbutton is housed.

Unfortunately, such a method has one major drawback due to the fact that, on the one hand, the dimensions of the torsion spring must be adapted to suit the dimensions of the object to be detected, which results in an additional set-up cost of the accommodating system and, on the other, it has been observed that the operation of the torsion spring, which consists in the transmission of the horizontal movement of the wings away from or towards one another in a vertical movement of the pushbutton, seriously deteriorates over time, to such an extent that this spring must frequently be replaced.

The weakening of the spring is all the more significant as the upper and lower wings of each flap become stiff with use. In fact, the stiffness of the wings stresses the spring more intensely to the extent that, on placing the object in the accommodating space, a first thrust force of the object generated by the contact of the object with each wing of each flap is directly transferred to the torsion spring which, over time, becomes weaker. A direct consequence of this weakening is that, on removing the object from its accommodating space, the torsion spring struggles to regain its rest state and the rise of the pushbutton is slowed down or even ineffective, which poses a particular problem when the device is used for applications that require a monitoring of movement in real time.

Typically, the increased stiffness of the flaps is caused, for example, by oxidation over time of the originally flexible polymer material that constituted each wing, or by the fact that the device is intended to house vials containing a drug that must be kept in a cold chamber, said device therefore needing to be placed repeatedly, at least during loading, in this cold chamber.

Moreover, the use of a torsion spring makes the assembly of the accommodating system laborious as the person skilled in the art must ensure that the spring remains attached to each hook on each of the movable ends of the second wings when inserting the system in the housing and fitting the lugs present on each flap into the recesses provided in the housing.

Furthermore, it was found that, whenever a person skilled in the art used the state-of-the-art device and wanted to insert or remove the object from the accommodating space, if the object is rotated about an axis parallel to the direction of insertion or removal, the torsion spring can come out of its position and become unhooked from the wings, which means that the device must be used precisely and carefully.

BRIEF SUMMARY

The purpose of the disclosure is to overcome the drawbacks of the state of the art by providing a device for the automatic and instant detection of movement of an object that is simpler to use whilst having a longer life and being easier to manufacture.

To resolve this problem, according to the disclosure, a device is provided as described above, characterized in that said pressure means is a plate connected by means of at least one compression spring to at least one part of the bottom wall of the housing against which said at least one compression spring bears.

In fact, according to the present disclosure, the presence of the plate as a pressure means against which the two ends of the movable part bear enables the horizontal movement of the flaps away from or towards one another in a vertical downward or upward movement directly transmitted to the compression spring with which it cooperates.

In this way, when an object is accommodated in the accommodating space of the system according to the disclosure, it comes into contact with at least one zone of each of the movable parts that move away from one another. As the first ends of each movable part are fixed, each second end bears against the plate and exerts a first thrust force thereon which is set in vertical motion, between a high position and a low position, in the same direction of insertion as the object.

The low position is a first position corresponding to a first situation in which the object is accommodated in the accommodating space, and where the plate transmits the first thrust force to the compression spring so that the latter is in a first compression state.

The high position is a second position corresponding to a second situation in which the object is removed from the accommodating space, and where the plate releases the first thrust force exerted on the compression spring so that the latter is in a second rest state.

Conversely, when the object is removed from the accommodating space, the two movable ends move towards one another so that the first thrust force is cancelled. The compression spring, bearing against the bottom wall of the housing, passes from the first compression state to a second rest state and exerts a second thrust force on the plate so that the latter moves from the second to the first position.

The device according to the disclosure thus provides an accommodating system of which the assembly is easier and of which the robustness in use and in the accuracy of transmission of information regarding the accommodation or removal of the object is increased because the replacement of the torsion spring, deemed to be a source of problems both when assembling the system according to the disclosure and during its use, with an assembly comprising the compression spring and a plate cooperating with the latter and the flaps has surprisingly enabled the same basic functions as the state-of-the-art device to be obtained, i.e. the conversion of the displacement movements of the flaps into a vertical displacement movement of the pushbutton, while at the same time providing a device with a less complex assembly and with a greater use resistance.

According to different embodiments of the device according to the disclosure, which can be considered together or separately:

- each flap comprises a second movable part connected to the second end of the first movable part by a means of articulation, each second movable part having a first end connected to said means of articulation and a second fixed end connected by a first means of connection to said plate;
- said plate is arranged to move between said first position which is a low position corresponding to a first situation in which the object is accommodated in the accommodating space, and where the plate transmits the first thrust force to the compression spring so that the latter assumes a first compression state, and said second position which is a high position corresponding to a second situation in which the object is removed from the accommodating space, and where the plate releases the first thrust force exerted on the compression spring so that the latter assumes a second rest state;
- the device comprises a second compression spring, said pushbutton being integrally connected to the plate via a second connection means, said second compression spring being arranged between the pushbutton and a dorsal face of the plate, the pushbutton also being arranged to pass through an orifice present in the bottom wall of said housing;
- said first and/or second movable parts are made of a polymer material; and
- the device comprises at least one means of guiding the plate.

Other embodiments of the device according to the disclosure are indicated in the accompanying claims.

The disclosure also relates to an assembly comprising the device according to the disclosure and a pressure sensor arranged to come into contact with the pushbutton, said pressure sensor being connected to a processing unit designed to process a first signal emitted by the sensor when a contact is created between the pushbutton and the pressure sensor, and a second signal emitted by the sensor when said contact is broken.

Other embodiments of the assembly according to the disclosure are indicated in the accompanying claims.

The disclosure also covers an object accommodating system, said system being designed to be accommodated in a housing of a device for the automatic and instant detection of movements of an object, said system comprising a first and a second flap facing one another, each flap comprising a first movable part, the first movable parts being arranged so as to define between them an object accommodating space, each movable part having a first fixed end and bearing against at its second end a pressure means of a pushbutton arranged to move along a vertical axis between a first position corresponding to the placing of the object in the accommodating space causing the two ends to move away from one another, and a second position corresponding to the removal of the object from the accommodating space causing the two ends to move towards one another, the system being characterized in that said pressure means is a plate arranged to be connected via at least one first compression spring to at least one part of the bottom wall of said housing against which said at least one compression spring bears. According to different embodiments of the system according to the disclosure, which can be considered together or separately:

- each flap comprises a second movable part connected to the second end of the first movable part by an articulation means, each second movable part having a first end connected to said articulation means and a second fixed end connected by a first connection means to said plate;
- said plate is arranged to move between said first position which is a low position corresponding to a first situation in which the object is accommodated in the accommodating space, and where the plate transmits the first thrust force to the compression spring so that the latter assumes a first compression state, and said second position which is a high position corresponding to a second situation in which the object is removed from the accommodating space, and where the plate releases the first thrust force exerted on the compression spring so that the latter assumes a second rest state;
- the system comprises a second compression spring, said pushbutton is integrally connected to the plate via a second connecting means, said second compression spring is arranged between the pushbutton and a dorsal face of the plate, the pushbutton also being arranged to pass through an orifice present in the bottom wall of said housing; and
- said first and/or second movable parts are made of a polymer material.

Other embodiments of the accommodating system according to the disclosure are indicated in the accompanying claims.

BRIEF DESCRIPTION OF THE DRAWINGS

Further features and advantages of the disclosure will emerge from the following non-limiting description.

In these Figures, similar elements bear the same reference numerals.

DETAILED DESCRIPTION

Figure 1:
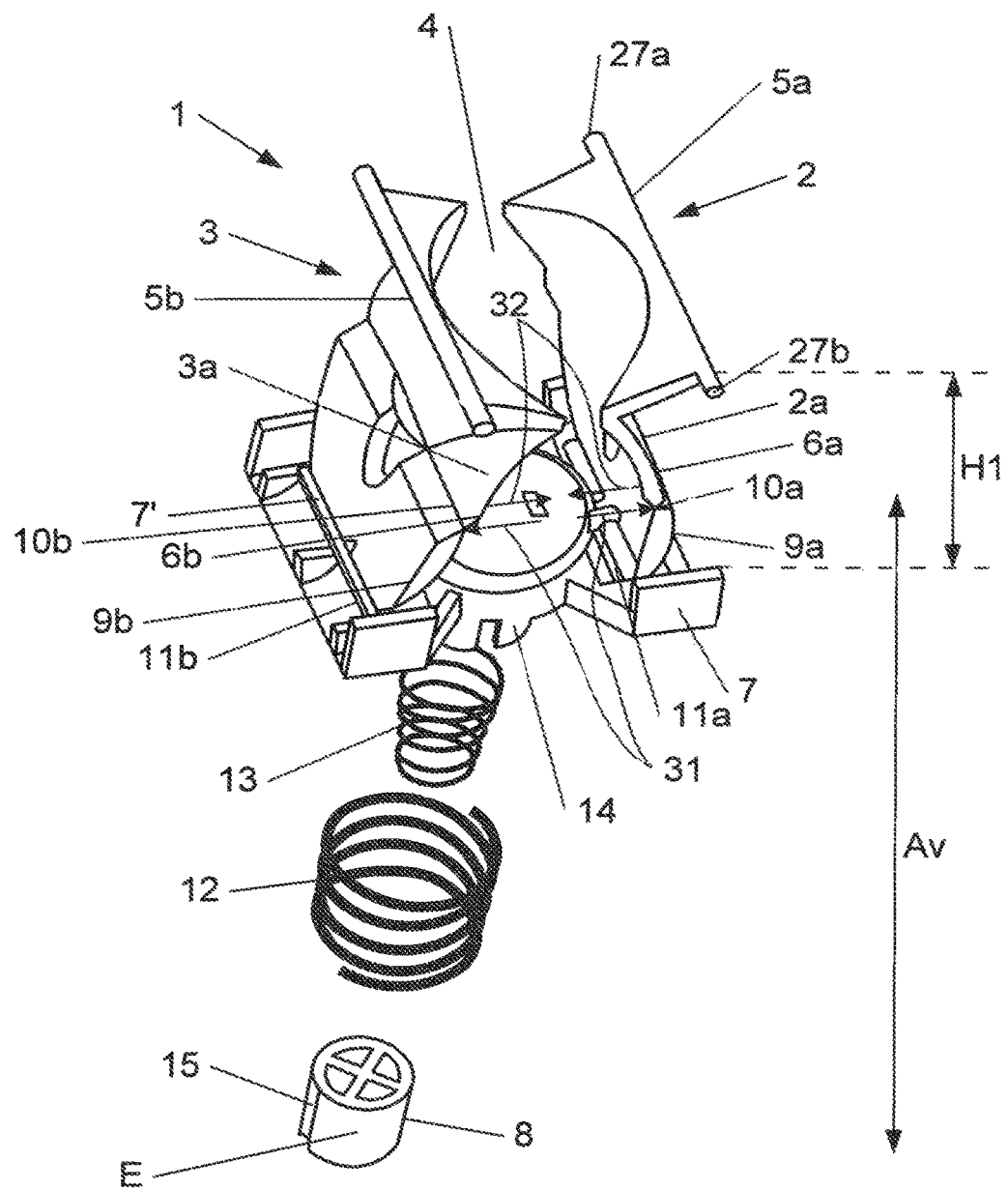
FIG. 1 is a partially exploded view of the object accommodating system according to the disclosure.

The accommodating system 1 according to the disclosure is illustrated in FIG. 1. As this Figure shows, the accommodating system 1 comprises a first 2 and a second 3 flap facing one another. Each flap also comprises a first movable part 2a, 3a that takes the form of a wing, the first movable parts 2a, 3a being arranged so as to define between them an object accommodating space 4.

Each movable first part 2a, 3a has a fixed first end 5a, 5b and a movable second end 6a, 6b that bears against a pressure means 7, which is a plate, of a pushbutton 8.

The movable first and second parts of each flap defining a length of flap that is the sum of a first length of movable first part and a second length of movable second part.

Each flap 1, 2 also comprises a movable second part 9a, 9b which takes the form of a wing and which is connected to the movable second end 6a, 6b of the movable first part 2a, 3a by an articulation means 10a, 10b which is for example a fold line present on each flap 1, 2 and formed between the first 2a, 3a and the second 9a, 9b movable parts of each flap 1, 2.

In the system as shown in FIG. 1, the movable second ends 6a, 6b of movable first parts 2a, 3a are directly connected via the fold line 10a, 10b of the flaps to the first ends of the movable second parts 9a, 9b so as to form two articulated flaps 1, 2, each movable second part 9a, 9b also having a fixed second end 11a, 11b connected by a first connection means to the plate 7.

The first connection means comprises a transverse slot present on an apical surface of the plate and in which the second end 11a, 11b is fitted, held fixed in the slot.

The plate 7 is arranged to be connected by means of a first compression spring 12 to the bottom wall of a housing, in which the accommodating system is designed to be inserted, the first compression spring 12 being arranged to bear against this bottom wall of the housing.

The accommodating system 1 also contains a second compression spring 13. The pushbutton is integrally connected to the plate 7 by means of a second connecting means 14, said second compression spring 13 being arranged between the pushbutton 8 and a dorsal face of the plate 7, opposite the apical face, the pushbutton also being arranged to pass through an orifice present in the bottom wall of the housing.

The second connecting means comprises a recess made in the dorsal face of the plate 7 and in which is inserted the second compression spring 13, connected at a first end to the plate and at a second end to the pushbutton 8.

The pushbutton 8 is arranged to move along a vertical axis $A_v$ between a first position corresponding to the placing of the object in the accommodating space causing the two movable ends 6a, 6b of the first movable parts 2a, 2b to move away from one another, and a second position corresponding to the removal of the object from the accommodating space causing the two movable ends 6a, 6b of the first movable parts 2a, 2b to move towards one another.

The pushbutton 8 is cylindrical in shape and comprises on its outer casing E at least one longitudinal slot 15 into which fits a lug present on an internal surface of the recess of a shape matching that of the pushbutton 8, the pushbutton 8 being free to move in a substantially vertical direction parallel to the direction of the longitudinal slot 15.

Preferably, the second compression spring 13 has a conical shape, the conicity of which is directed towards the second end of the second spring 13.

The plate preferably has at a first end a first pair of transverse slots and at a second end a second pair of transverse slots, the second end 11a, 11b of each second movable part 9a, 9b of the flap 2, 3 being designed to be fitted into one of the slots of each pair of slots. Preferably, the two slots of a pair of slots are separated by an edge 7' protruding from the apical face of the plate 7.

Advantageously, the first and/or second movable parts are made of a polymer material.

Figure 2:
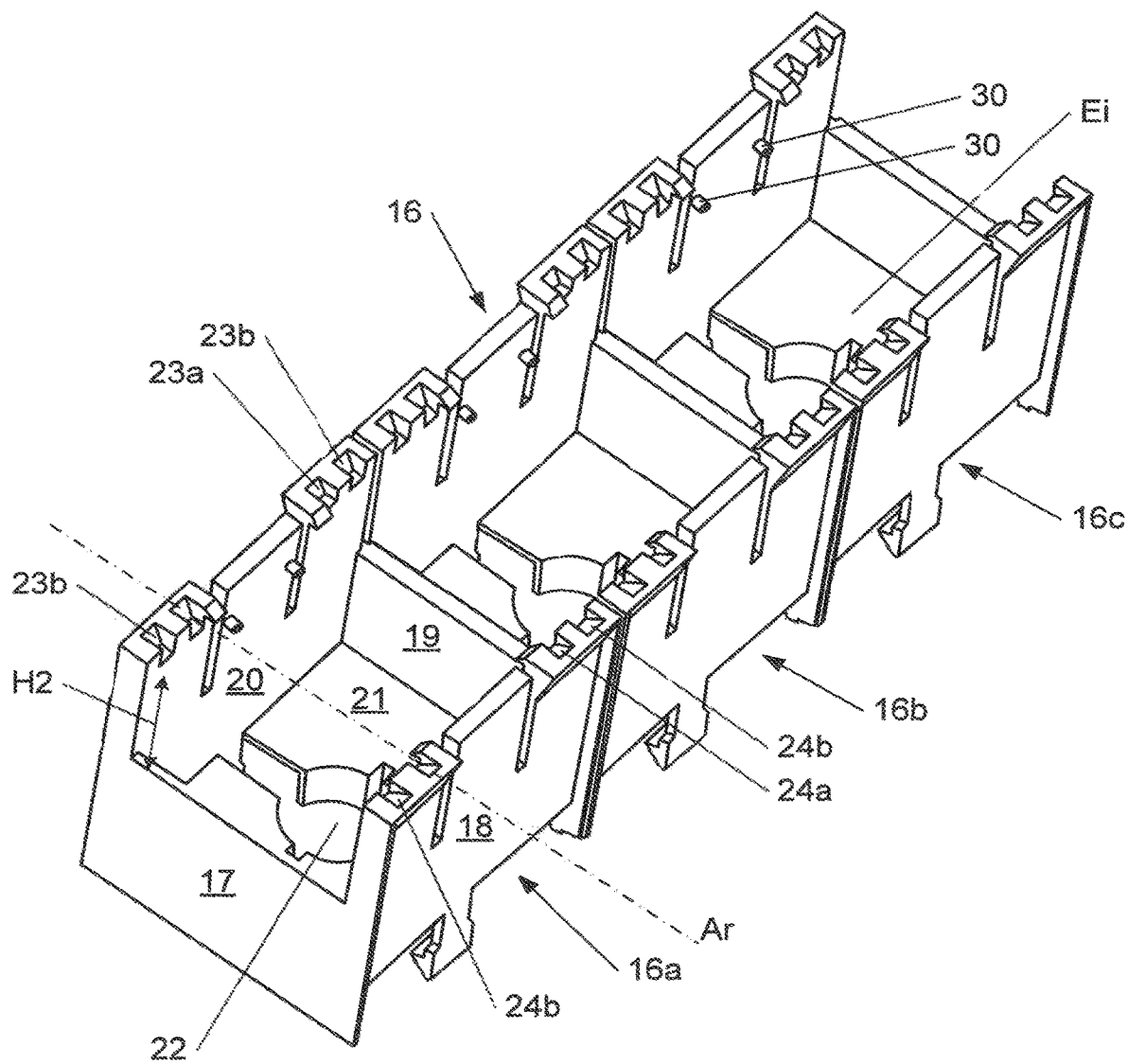
FIG. 2 represents a particular embodiment of the housing of the device according to the disclosure.
Figure 3:
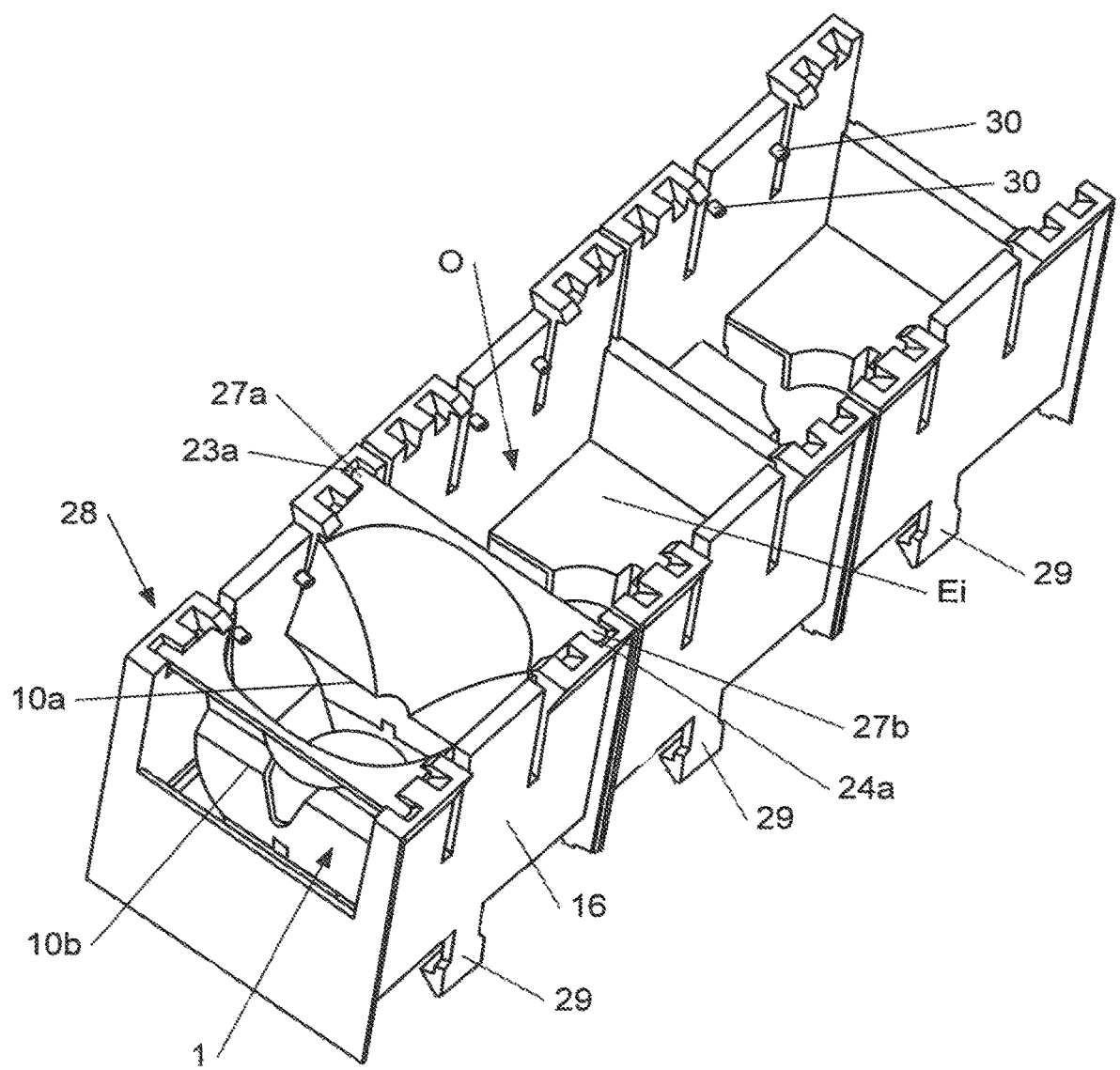
FIG. 3 represents a particular embodiment of the device according to the disclosure in which the accommodating system of FIG. 1 is accommodated in the housing of FIG. 2.

FIG. 2 shows a preferred embodiment of a housing in which the accommodating system 1 is designed to be inserted in order to form the device shown in FIG. 3.

The housing 16 as shown in FIG. 2 is formed of a plurality of housings 16a, 16b, 16c, each housing being defined by four side walls 17, 18, 19, 20 connected to and projecting from the bottom wall 21 that has an orifice 22 arranged to be passed through by the pushbutton 8.

The housing has at least one pair of recesses 23a, 24a and 23b, 24b, each recess of each pair being opposite one another. Typically, for each pair of recesses, a first recess 23a is arranged on a first free edge of a first side wall 20 while a second recess 24a is arranged on a second free edge of a second side wall 18, said second side wall 18 facing the first side wall 20.

The first fixed end 5a, 5b of each movable first part 2a, 3a of each flap 2, 3, has a pair of lugs 27a, 27b (see FIG. 1) arranged to be inserted in each of the recesses 23a, 24a of the pair of recesses, so that the first fixed end 5a, 5b is connected to the housing in such a way that each movable first part 2a, 3a can be made to rotate about a first axis of rotation $A_r$ passing through each recess 23a, 24a of the pair of recesses.

FIG. 3 is a perspective view of the device 28 according to the disclosure comprising the accommodating system 1 and the housing 16.

As this Figure shows, the four side walls 17, 18, 19, 20 form an access opening O to an internal space $E_i$ of the housing arranged to be passed through by the accommodating system 1 when the latter is inserted in the housing and is accommodated in the internal space $E_i$.

Once the accommodating system is placed in the internal space $E_i$ of the housing, the object can be inserted directly into the internal accommodating space of the accommodating system through the access opening O of the housing 16.

The device is provided at its base with connection means 29, which are tabs projecting in a direction opposite to that of the access opening of the housing and arranged to be fitted into a plurality of female sockets present in a movement sensor so as to form an assembly (not shown), said pressure sensor being connected to a processing unit (not shown) designed to process a first signal emitted by the sensor when a contact is created between the pushbutton 8 and the pressure sensor, and a second signal emitted by the sensor when the contact is broken.

During operation, when an object is accommodated in the accommodating space of the accommodating system 1, it comes into contact with at least one zone of each of the movable first parts 2a, 3a which move away from one another (arrows 31, FIG. 1).

As the first ends 5a, 5b of each movable first part 2a, 3a are fixed, when the movable first parts 2a, 3a move away from one another in a rotational movement defined by the axis of rotation $A_r$ in order to accommodate the object, each movable second end 6a, 6b that bears against the plate 7 by means of each movable second part 9a, 9b, move away from one another and a vertical movement of each second end 11a, 11b of each movable second part 9a, 9b connected to the plate 7 is generated so that these second ends 11a, 11b exert a first thrust force on the plate 7 which is set in vertical motion, between a high position and a low position, in the same direction of insertion as the object parallel to the vertical axis $A_v$.

The pushbutton then moves in the direction of the pressure sensor until it comes into contact therewith, each first fixed end 5a, 5b of each first movable part 2a, 3a and the plate being separated by a predetermined height H1 (see FIG. 1) so that when the plate is in its low position, the pushbutton is in contact with the sensor.

Typically, in the accommodating system 1, a first predetermined distance from the high position of the plate 7 and the position of the movement sensor is below or equal to the length of the flaps.

The pushbutton 8 coming into contact with the sensor causes the emission of a first electrical impulse indicating that this introduction movement has occurred and, consequently, that this object is present in the accommodating space, said first impulse being processed by a processing means arranged to convert this first impulse into a signal indicating that the object is present in the accommodating space.

When it comes into contact with the movement sensor, the pushbutton 8 exerts thereon a vertical pressure that is partly absorbed by the second compression spring 13, the button 8 re-entering the recess on the dorsal face of the plate 7.

In this context, the second compression spring 19 serves not only to absorb the vertical pressure generated by the pushbutton on the movement sensor, which is usually a resistive sensor, which vertical pressure can differ depending on the size (and therefore the diameter) of the object inserted in the accommodating space of the accommodating system, but also thus to prevent the resistive sensor from wearing too quickly.

Similarly, the presence of this second compression spring makes it possible to generate a second thrust force that is exerted on the dorsal face of the plate 7, from the low position to the high position, when the object is removed from the accommodating space. This second thrust force thus enables the plate to resume its initial high position more easily and without the influence of wear of the plastics material constituting the device, particularly the plate and the side walls of the housing, over time.

Preferably, the plate 7 is held in its high position by the presence of at least one side lug located on an inner face of a side wall of the housing and arranged to be in contact with the plate.

Conversely, when the object is removed from the accommodating space, the two movable ends 6a, 6b move towards one another (arrows 31, FIG. 1) so that the first thrust force is cancelled out. The compression spring 12, bearing against the bottom wall 21 of the housing 16, passes from the first compression state to a second rest state and exerts a second thrust force on the plate 7 so that the latter moves from the low position to the high position.

On removing the object from the accommodating system 1, while the pushbutton 8 is in contact with the resistive sensor, the second compression spring 13 provides the maximum thrust and contributes, together with the thrust effort of the first compression spring 12, to the generation of the vertical translational movement of the plate from its low position to its high position.

Then, as soon as the contact between the pushbutton 8 and the resistive sensor is broken, the plate moves to its high position under the influence of the first compression spring.

In the context of the present disclosure, the words "low position" define a first position corresponding to a first situation in which the object is accommodated in the accommodating space, and where the plate 7 transmits the first thrust force to the first compression spring 9 so that the latter is in a first compression state.

The words "high position" define a second position corresponding to a second situation in which the object is removed from the accommodating space, and where the plate releases the first thrust force exerted on the compression spring so that the latter is in a second rest state.

The pushbutton 8 then moves away from the sensor causing the emission of a second electrical impulse indicating that this removal movement has occurred and, consequently, that this object is absent from the accommodating space, said second impulse being processed by the processing means arranged to convert this second impulse into a signal indicating the absence of the object in the accommodating space.

These electrical impulses, which constitute information on the movements of these objects, can be transmitted, depending on requirements, via a smart card and for example a Wi-Fi network, for example to a computer processing unit for their use by the appropriate software.

It should be noted that at any time during the vertical displacement of the plate 7, the movement thereof is guided by the presence of the side walls 18, 19, 20, 21 of the housing 16.

Depending on the size of the object to be inserted in the accommodating space, the lugs 27a, 27b of each flap 2, 3 are inserted into each of the recesses of the first pair 23a, 24a of recesses or into each of the recesses of the second pair 23b, 24b of recesses so as to modulate the accommodating volume defining the accommodating space in order to facilitate insertion of the object. Thus, for a large object, i.e. with a diameter of between 15 mm and 30 mm for example, it is preferable to have an accommodating volume that is as large as possible to facilitate the entry of this object into the accommodating space.

By contrast, for objects of smaller diameter, i.e. between 10 mm and 14 mm for example, it is preferable to reduce the accommodating volume defining the accommodating space so that the object can come into contact with the flap walls more easily.

The insertion of the object, whatever its size, can also be facilitated by having movable first parts 2a, 3a of flap 2, 3 that each have a concave apical face so as to form, when the plate is in its second position, a funnel-shaped recess.

Moreover, the second fixed end 11a, 11b of each of the movable second parts 9a, 9b is inserted in one or other slot of a pair of slots present on the plate 7 so as to modulate the amplitude of vertical movement of the second fixed end 11a, 11b connected to the plate.

The side walls to which the flaps 2, 3 are connected can also have on their internal face defining the internal space $E_i$ of the housing at least one lug 30 projecting from the internal face in the direction of the internal space $E_i$ (FIGS. 2 and 3). These lugs 30 are typically arranged so as to limit the rotational movement of each first movable part 2a, 3a of each flap 2, 3 and to define a sufficient distance between the fold lines 10a and 10b so as to provide an accommodating space defined by a sufficiently large accommodating volume when the plate 7 is in its second position in order to facilitate the insertion of the object.

Although the description relates to a preferred embodiment of the device according to the disclosure in which each flap comprises two movable parts articulated to one another, it is understood that the present disclosure is not limited to these characteristics but also covers other embodiments involving an accommodating system comprising a first and a second flap facing one another, each flap comprising at least one first movable part.

Furthermore, it must be understood that the present disclosure can also cover a specific embodiment of the accommodating system, and the device that comprises this accommodating system, in which the two flaps each comprise a movable part, the first movable parts bearing at their second end against the pressure means of the pushbutton.

Of course, the present disclosure is in no way limited to the embodiments described above and modifications can be made thereto without departing from the scope of the accompanying claims.

The invention claimed is:

1. A device for automatic and instant detection of movements of an object, said device comprising:
a housing;
an object accommodating system arranged in the housing comprising a first and a second flap facing one another, each flap comprising a first movable part, the first movable parts being arranged so as to define between one another an object accommodating space, each movable part having a first fixed end and a second fixed end, the second ends bearing against a pressure means for pressing a pushbutton, the pushbutton arranged to move along a vertical axis between a first position corresponding to the placing of an object in the accommodating space causing the second ends to move away from one another, and a second position corresponding to the removal of the object from the accommodating space causing the second ends to move towards one another,
wherein the pressure means is a plate connected by means of at least one compression spring to at least one part of a bottom wall of said housing against which said at least one compression spring bears.

2. The device according to claim 1, wherein said first movable parts are made of a polymer material.

3. The device according to claim 1, wherein each flap comprises a second movable part connected to the second end of the first movable part by an articulation means, each second movable part having a first end connected to said articulation means and a second fixed end connected by a first connection means to said plate.

4. The device according to claim 3, wherein said second movable parts are made of a polymer material.

5. The device according to claim 1, wherein said plate is arranged to move between said first position which is a low position corresponding to a first situation in which the object is accommodated in the accommodating space, and where the plate transmits a first thrust force to the compression spring so that the compression spring assumes a first compression state, and said second position which is a high position corresponding to a second situation in which the object is removed from the accommodating space, and where the plate releases the first thrust force exerted on the compression spring so that the compression spring assumes a second rest state.

6. The device according to claim 1, further comprising a second compression spring, said pushbutton being integrally connected to the plate via a second connection means, said second compression spring being arranged between the pushbutton and a dorsal face of the plate, the pushbutton also being arranged to pass through an orifice present in the bottom wall of said housing (16).

7. The device according to claim 1, further comprising at least one guiding means for guiding the plate.

8. An assembly comprising the device according to claim 1, wherein a pressure sensor is arranged to come into contact with the pushbutton, said pressure sensor being connected to a processing unit designed to process a first signal emitted by the sensor when a contact is created between the pushbutton and the pressure sensor, and a second signal emitted by the sensor when said contact is broken.

9. An object accommodating system, said system being designed to be accommodated in a housing of a device for the automatic and instant detection of movements of an object, said system comprising a first and a second flap facing one another, each flap comprising a first movable part, the first movable parts being arranged so as to define between them an object accommodating space, each of the first movable parts having a first fixed end and a second end, the second ends bearing against a pressure means for pressing a pushbutton, the pushbutton arranged to move along a vertical axis between a first position corresponding to the placing of the object in the accommodating space causing the second ends to move away from one another, and a second position corresponding to the removal of the object from the accommodating space causing the second ends to move towards one another, wherein said pressure means is a plate arranged to be connected via at least one first compression spring to at least one part of a bottom wall of said housing against which said at least one compression spring bears.

10. The system according to claim 9, wherein said first movable parts are made of a polymer material.

11. The system according to claim 9, wherein each flap comprises a second movable part connected to the second end of the first movable part by an articulation means, each second movable part having a first end connected to said articulation means and a second fixed end connected by a first connection means to said plate.

12. The system according to claim 11, wherein said second movable parts are made of a polymer material.

13. The system according to claim 9, wherein said plate is arranged to move between said first position which is a low position corresponding to a first situation in which the object is accommodated in the accommodating space, and where the plate transmits the first thrust force to the compression spring so that the compression spring assumes a first compression state, and said second position which is a high position corresponding to a second situation in which the object is removed from the accommodating space, and where the plate releases the first thrust force exerted on the compression spring so that the compression spring assumes a second rest state.

14. The system according to claim 9, further comprising a second compression spring, said pushbutton being integrally connected to the plate via a second connection means, said second compression spring being arranged between the pushbutton and a dorsal face of the plate, the pushbutton also being arranged to pass through an orifice present in the bottom wall of said housing.

* * * * *